(12) United States Patent
Batard et al.

(10) Patent No.: US 6,787,337 B1
(45) Date of Patent: Sep. 7, 2004

(54) RECORDING OF DNA SEQUENCES TO ENABLE THEM TO BE EXPRESSED IN YEASTS, AND THE TRANSFORMED YEASTS OBTAINED

(75) Inventors: Yannick Batard, Strasbourg (FR); Francis Durst, Bernolsheim (FR); Michel Schalk, Hutteheim (FR); Daniele Werck-Reichhart, Dingsheim (FR)

(73) Assignee: Aventis CropScience S.A., Lyons (FR)

( * ) Notice: Subject to any disclaimer, the term of this patent is extended or adjusted under 35 U.S.C. 154(b) by 0 days.

(21) Appl. No.: 09/713,794

(22) Filed: Nov. 15, 2000

Related U.S. Application Data

(63) Continuation of application No. 09/158,767, filed on Sep. 23, 1998, now Pat. No. 6,180,363.

(30) Foreign Application Priority Data

Sep. 24, 1997 (FR) .............................. 97 12094

(51) Int. Cl.[7] ............................... C12P 21/00
(52) U.S. Cl. .................... 435/71.1; 435/69.1; 435/91.1; 435/320.1; 435/471; 435/254.2; 536/23.1
(58) Field of Search ............... 435/71.1, 69.1, 435/91.1, 320.1, 471, 254.2; 536/23.1

(56) References Cited

U.S. PATENT DOCUMENTS 5,096,825 A    3/1992   Barr et al. ............... 435/254.2
6,180,363 B1 * 1/2001   Batard et al. .............. 435/69.1

FOREIGN PATENT DOCUMENTS

EP    0255233     2/1998
FR    2693207     1/1994
GB    2216530    10/1989
WO    9401564     1/1994

OTHER PUBLICATIONS

Hoekema et al. Molecular and Cellular Biology 7:2914–2924 1987.*
Neill et al. Gene 55:303–317 1987.*
Kotula et al. Evaluation of foreign gene codon optimization in yeast: expression of a mouse IG Kappa chain. Dec. 1991. Biotechnology (N.Y.); 9(12):1386–9.*
Skaggs et al. Gene 169:105–109 1996.*
Fang et al. (1989) J. Biol. Chem 271: 16460.
Murray et al. (1989) Nucleic Acids Res. 17:477.
Skaggs et al. (1996) Gene 169:105.
GenBank Accession No. X87611.
Yasukazu Nakamura, "Codon usage database", GenBank Release 128.0, Feb. 15, 2002, http://www.kazusa.or.jp/codon/.

* cited by examiner

Primary Examiner—James Ketter
Assistant Examiner—David A. Lambertson
(74) Attorney, Agent, or Firm—Baker Botts L.L.P.

(57) ABSTRACT

The present invention relates to a recombinant non-yeast DNA, which encodes a protein of interest, wherein an unmodified DNA corresponding to the recombinant non-yeast DNA contains a region having a high content of codons that are poorly suited to yeasts, wherein a number of the codons that are poorly suited to yeasts are replaced in said region of the recombinant non-yeast DNA with synonymous codons coding for the same amino acid that are well-suited to yeasts, and wherein the number of replaced codons is sufficient to permit expression in yeasts. The present invention also relates to DNA sequences which originate from dicotyledonous or monocotyledonous plants, and in particular plants of the graminae family which are selected from among wheat, barley, oats, rice, maize, sorghum and cane sugar, as well as to vectors and transformed yeasts which contain the DNA sequences of the invention.

26 Claims, No Drawings

SEQUENCE LISTING

<160> NUMBER OF SEQ ID NOS: 20

<210> SEQ ID NO 1
<211> LENGTH: 2261
<212> TYPE: DNA
<213> ORGANISM: Triticum aestivum

<400> SEQUENCE: 1

```
cgcagcacgg caacacatac acaggagcca cacaccgcac ctacccgat ggacgtcctc      60 ctcctggaga aggccctcct gggcctcttc gccgcggcg tgctggccat cgccgtcgcc     120
aagctcaccg gcaagcgctt ccgcctcccc cctggcccct ccggcgcccc catcgtcggc     180
aactggctgc aggtcggcga cgacctcaac caccgcaacc tgatgggcct ggccaagcgg     240
ttcggcgagg tgttcctcct ccgcatgggc gtccgcaacc tggtggtcgt ctccagcccc     300
gagctcgcca aggaggtcct ccacacccag ggcgtcgagt tcggctcccg cacccgcaac     360
gtcgtcttcg acatcttcac cggcaaggga caggacatgg tgttcacggt gtacggcgac     420
cactggcgca agatgcggcg gatcatgacg gtgcccttct tcaccaacaa ggtggtggcg     480
cagaaccgcg tggggtggga ggaggaggcc cggctggtgg tggaggacct caaggccgac     540
ccggcggcgg cgacggcggg cgtggtggtc cgccgcaggc tgcagctcat gatgtacaac     600
gacatgttcc gcatcatgtt cgaccgccgg ttcgagagcg tggccgaccc gctcttcaac     660
cagctcaagg cgctcaacgc cgagcgcagc atcctctccc agagcttcga ctacaactac     720
ggcgacttca tccccgtcct ccgccccttc ctccgccgct acctcaaccg ctgcaccaac     780
ctcaagacca agcggatgaa ggtgttcgag gaccacttcg tccagcagcg caaggaggcg     840
ttggagaaga cgggtgagat caggtgcgcc atggaccaca tcctggaagc cgaaaggaag     900
ggcgagatca accacgacaa cgtcctctac atcgtcgaga acatcaacgt cgcagccatc     960
gagacgacgc tgtggtcgat cgagtggggc ctcgcggagc tggtgaacca cccggagatc    1020
cagcagaagc tgcgcgagga gatcgtcgcc gttctgggcg ccggcgtggc ggtgacggag    1080
ccggacctgg agcgcctccc ctacctgcag tccgtggtga aggagacgct ccgcctccgc    1140
atggcaatcc cgctcctggt gccgcacatg aacctcagcg acgccaagct cgccggctac    1200
gacatccccg ccgagtccaa gatcctcgtc aacgcctggt tcctcgccaa cgaccccaag    1260
cggtgggtgc gcgccgatga gttcaggccg gagaggttcc tcgaggagga gaaggccgtc    1320
gaggcccacg gcaacgattt ccggttcgtg cccttcggcg tcggccgccg gagctgcccc    1380
gggatcatcc tcgcgctgcc catcatcggc atcacgctcg gacgcctggt gcagaacttc    1440
cagctgctgc cgccgccggg gcaggacaag atcgacacca ccgagaagcc cgggcagttt    1500
accaaccaga tcctcaagca cgccaccatt gtctgcaagc cactcgaggc ttaactgaat    1560
tgaggtttcg gtcatgggcg cccgctgacg cggggagatg gatctatgca tgtgactgtg    1620
tattttgcct tctttctttt tggtgttgtt ttttgcagta gtaagtttaa tttttctttg    1680
```

-continued

```
gtgttggcct atttgtcttc atgtgaggcg tcgtgttgta aatttccata tagttggcaa      1740
tgtgatgtaa aacttggctc caaaaaaaaa aaaaaaaaac tcgagactct tctctctctc      1800
tctctctctc cagcctcggg tctctgctgg caagggaact tgcattaccc tgtgtacgac      1860
ggcgccatgt tcgtccctga agcaccctcc ctgcagagct cccaggacaa cttcgctgca      1920
tctgctggtt tcaagcgtcg aaggagagag ttttgaatac ccgaaagaat atagcgttgg      1980
acatatctgt caaacagggg atcttgctgt gggtctcttg gtgggccaaa tcgcatagac      2040
aatcattcaa atggatgggt tcttcgctgg tcggtcaaaa agtatatgtt gtaattgtac      2100
gccttttttg ggtcttgttg ccaaagatca tggttattga gttgtgagct ctgagataac      2160
aggtttgtgt atagtgaaat aaagaggagc gtcgtcaaca ccatgtacta tataggcttt      2220
gaaattccat taagatgcat cagaaatcaa tgttggattt g                         2261
```

<210> SEQ ID NO 2
<211> LENGTH: 38
<212> TYPE: DNA
<213> ORGANISM: Artificial Sequence
<220> FEATURE:
<223> OTHER INFORMATION: :

<400> SEQUENCE: 2

```
atatatggat ccatggacgt cctcctcctg gagaaggc                              38
```

<210> SEQ ID NO 3
<211> LENGTH: 56
<212> TYPE: DNA
<213> ORGANISM: Artificial Sequence
<220> FEATURE:
<223> OTHER INFORMATION: :

<400> SEQUENCE: 3

```
atatatggat ccatggatgt tttgttgttg gagaaggccc tcctgggcct cttcgc          56
```

<210> SEQ ID NO 4
<211> LENGTH: 71
<212> TYPE: DNA
<213> ORGANISM: Artificial Sequence
<220> FEATURE:
<223> OTHER INFORMATION: :

<400> SEQUENCE: 4

```
atatatggat ccatggatgt tttgttgttg gaaaaagctt tgttgggttt gttcgccgcg      60
gcggtgctgg c                                                           71
```

<210> SEQ ID NO 5
<211> LENGTH: 143
<212> TYPE: DNA
<213> ORGANISM: Artificial Sequence
<220> FEATURE:
<223> OTHER INFORMATION: :

<400> SEQUENCE: 5

```
atatatggat ccatggatgt tttgttgttg gaaaaagctt tgttgggttt gtttgctgct      60
gctgttttgg ctattgctgt tgctaaattg actggtaaaa gatttagatt gccaccaggt     120
ccatccggcg cccccatcgt cgg                                             143
```

<210> SEQ ID NO 6
<211> LENGTH: 39
<212> TYPE: DNA
<213> ORGANISM: Artificial Sequence

```
<220> FEATURE:
<223> OTHER INFORMATION: :

<400> SEQUENCE: 6
tatatagaat tccagttaag cctcgagtgg cttgcagac                    39

<210> SEQ ID NO 7
<211> LENGTH: 1506
<212> TYPE: DNA
<213> ORGANISM: Artificial Sequence
<220> FEATURE:
<223> OTHER INFORMATION: :

<400> SEQUENCE: 7
atggatgttt tgttgttgga gaaggccctc ctgggcctct tcgccgcggc ggtgctggcc    60
atcgccgtcg ccaagctcac cggcaagcgc ttccgcctcc ccctggccc ctccggcgcc   120
cccatcgtcg gcaactggct gcaggtcggc gacgacctca accaccgcaa cctgatgggc   180
ctggccaagc ggttcggcga ggtgttcctc ctccgcatgg gcgtccgcaa cctggtggtc   240
gtctccagcc ccgagctcgc caaggaggtc ctccacaccc agggcgtcga gttcggctcc   300
cgcacccgca acgtcgtctt cgacatcttc accggcaagg acaggacat ggtgttcacg   360
gtgtacggcg accactggcg caagatgcgc cggatcatga cggtgccctt cttcaccaac   420
aaggtggtgg cgcagaaccg cgtgggggtgg aggaggagg cccggctggt ggtggaggac   480
ctcaaggccg acccgcggc ggcgacggcg ggcgtggtgg tccgccgcag gctgcagctc   540
atgatgtaca cgacatgtt ccgcatcatg ttcgaccgcc ggttcgagag cgtggccgac   600
ccgctcttca accagctcaa ggcgctcaac gccgagcgca gcatcctctc ccagagcttc   660
gactacaact acgcgactt catccccgtc ctccgcccct tcctccgccg ctacctcaac   720
cgctgcacca acctcaagac caagcggatg aaggtgttcg aggaccactt cgtccagcag   780
cgcaaggagg cgttggagaa gacgggtgag atcaggtgcg ccatggacca catcctggaa   840
gccgaaagga agggcgagat caaccacgac aacgtcctct acatcgtcga gaacatcaac   900
gtcgcagcca tcgagacgac gctgtggtcg atcgagtggg gcctcgcgga gctggtgaac   960
caccgggaga tccagcagaa gctgcgcgag gagatcgtcg ccgttctggg cgccggcgtg  1020
gcggtgacgg agccggacct ggagcgcctc ccctacctgc agtccgtggt gaaggagacg  1080
ctccgcctcc gcatggcaat cccgctcctg gtgccgcaca tgaacctcag cgacgccaag  1140
ctcgccggct acgacatccc cgccgagtcc aagatcctcg tcaacgcctg gttcctcgcc  1200
aacgacccca gcggtgggt gcgcgccgat gagttcaggc cggagaggtt cctcgaggag  1260
gagaaggccg tcgaggccca cggcaacgat ttccggttcg tgcccttcgg cgtcggccgc  1320
cggagctgcc ccgggatcat cctcgcgctg cccatcatcg gcatcacgct cggacgcctg  1380
gtgcagaact tccagctgct gccgccgccg gggcaggaca agatcgacac caccgagaag  1440
cccgggcagt ttaccaacca gatcctcaag cacgccacca ttgtctgcaa gccactcgag  1500
gcttaa                                                            1506

<210> SEQ ID NO 8
<211> LENGTH: 1506
<212> TYPE: DNA
<213> ORGANISM: Artificial Sequence
<220> FEATURE:
<223> OTHER INFORMATION: :

<400> SEQUENCE: 8
```

```
atggatgttt tgttgttgga aaaagctttg ttgggtttgt tcgccgcggc ggtgctggcc        60
atcgccgtcg ccaagctcac cggcaagcgc ttccgcctcc ccctggccc ctccggcgcc       120
cccatcgtcg gcaactggct gcaggtcggc gacgacctca accaccgcaa cctgatgggc       180
ctggccaagc ggttcggcga ggtgttcctc ctccgcatgg gcgtccgcaa cctggtggtc       240
gtctccagcc ccgagctcgc caaggaggtc ctccacaccc agggcgtcga gttcggctcc       300
cgcacccgca acgtcgtctt cgacatcttc accggcaagg acaggacat ggtgttcacg       360
gtgtacggcg accactggcg caagatgcgg cggatcatga cggtgcccct cttcaccaac       420
aaggtggtgg cgcagaaccg cgtggggtgg aggaggagg cccggctggt ggtggaggac       480
ctcaaggccg acccggcggc ggcgacggcg ggcgtggtgg tccgccgcag gctgcagctc       540
atgatgtaca cgacatgtt ccgcatcatg ttcgaccgcc ggttcgagag cgtggccgac       600
ccgctcttca accagctcaa ggcgctcaac gccgagcgca gcatcctctc ccagagcttc       660
gactacaact acgcgactt catcccgtc ctccgccct cctccgccg ctacctcaac          720
cgctgcacca acctcaagac caagcggatg aaggtgttcg aggaccactt cgtccagcag       780
cgcaaggagg cgttggagaa gacgggtgag atcaggtgcg ccatggacca catcctggaa       840
gccgaaagga agggcgagat caaccacgac aacgtcctct acatcgtcga gaacatcaac       900
gtcgcagcca tcgagacgac gctgtggtcg atcgagtggg gcctcgcgga gctggtgaac       960
cacccggaga tccagcagaa gctgcgcgag gagatcgtcg ccgttctggg cgccggcgtg      1020
gcggtgacgg agccggacct ggagcgcctc ccctacctgc agtccgtggt gaaggagacg      1080
ctccgcctcc gcatggcaat cccgctcctg gtgccgcaca tgaacctcag cgacgccaag      1140
ctcgccggct acgacatccc cgccgagtcc aagatcctcg tcaacgcctg gttcctcgcc      1200
aacgacccca gcggtgggt gcgcgccgat gagttcaggc cggagaggtt cctcgaggag      1260
gagaaggccg tcgaggccca cggcaacgat ttccggttcg tgcccttcgg cgtcggccgc      1320
cggagctgcc ccgggatcat cctcgcgctg cccatcatcg gcatcacgct cggacgcctg      1380
gtgcagaact tccagctgct gccgccgccg gggcaggaca agatcgacac caccgagaag      1440
cccgggcagt ttaccaacca gatcctcaag cacgccacca ttgtctgcaa gccactcgag      1500
gcttaa                                                                 1506
```

<210> SEQ ID NO 9
<211> LENGTH: 1506
<212> TYPE: DNA
<213> ORGANISM: Artificial Sequence
<220> FEATURE:
<223> OTHER INFORMATION: :

<400> SEQUENCE: 9

```
atggatgttt tgttgttgga aaaagctttg ttgggtttgt ttgctgctgc tgttttggct        60
attgctgttg ctaaattgac tggtaaaaga tttagattgc caccaggtcc atccggcgcc       120
cccatcgtcg gcaactggct gcaggtcggc gacgacctca accaccgcaa cctgatgggc       180
ctggccaagc ggttcggcga ggtgttcctc ctccgcatgg gcgtccgcaa cctggtggtc       240
gtctccagcc ccgagctcgc caaggaggtc ctccacaccc agggcgtcga gttcggctcc       300
cgcacccgca acgtcgtctt cgacatcttc accggcaagg acaggacat ggtgttcacg       360
gtgtacggcg accactggcg caagatgcgg cggatcatga cggtgcccct cttcaccaac       420
aaggtggtgg cgcagaaccg cgtggggtgg aggaggagg cccggctggt ggtggaggac       480
ctcaaggccg acccggcggc ggcgacggcg ggcgtggtgg tccgccgcag gctgcagctc       540
```

-continued

```
atgatgtaca acgacatgtt ccgcatcatg ttcgaccgcc ggttcgagag cgtggccgac      600
ccgctcttca accagctcaa ggcgctcaac gccgagcgca gcatcctctc ccagagcttc      660
gactacaact acggcgactt catccccgtc ctccgcccct tcctccgccg ctacctcaac      720
cgctgcacca acctcaagac caagcggatg aaggtgttcg aggaccactt cgtccagcag      780
cgcaaggagg cgttggagaa gacgggtgag atcaggtgcg ccatggacca catcctggaa      840
gccgaaagga agggcgagat caaccacgac aacgtcctct acatcgtcga aacatcaac      900
gtcgcagcca tcgagacgac gctgtggtcg atcgagtggg gcctcgcgga gctggtgaac      960
caccccggaga tccagcagaa gctgcgcgag gagatcgtcg ccgttctggg cgccggcgtg     1020
gcggtgacgg agccggacct ggagcgcctc ccctacctgc agtccgtggt gaaggagacg     1080
ctccgcctcc gcatggcaat cccgctcctg gtgccgcaca tgaacctcag cgacgccaag     1140
ctcgccggct acgacatccc cgccgagtcc aagatcctcg tcaacgcctg gttcctcgcc     1200
aacgacccca gcggtgggt gcgcgccgat gagttcaggc cggagaggtt cctcgaggag      1260
gagaaggccg tcgaggccca cggcaacgat tccggttcg tgcccttcgg cgtcggccgc      1320
cggagctgcc ccgggatcat cctcgcgctg cccatcatcg gcatcacgct cggacgcctg     1380
gtgcagaact tccagctgct gccgccgccg gggcaggaca agatcgacac caccgagaag     1440
cccgggcagt ttaccaacca gatcctcaag cacgccacca ttgtctgcaa gccactcgag     1500
gcttaa                                                                1506
```

<210> SEQ ID NO 10
<211> LENGTH: 2181
<212> TYPE: DNA
<213> ORGANISM: Triticum aestivum

<400> SEQUENCE: 10

```
cgatccaccc cttggatcca ctctacccag ctcgctagcc agcggggtac atacacgcac       60
gcacgtacgc gcgtacgtac actcgcagag cttgcttcag ggaggccggc aatggaggtg      120
gggacgtggg cggtggtggt gtcggcggtg gccgcgtaca tggcgtggtt ctggcggatg      180
tcccgcgggc tgcgcgggcc gcgggttttgg cccgtgctcg gcagcctgcc gggcctggtg     240
cagcacgccg aggacatgca cgagtggatc gccggcaacc tgcgccgcgc gggcggcacg      300
taccagacct gcatcttcgc cgtgcccggg gtggcgcgcc gcggcggcct ggtcaccgtc      360
acctgcgacc cgcgcaacct ggagcacgtc ctgaaggcgc gcttcgacaa ctaccccaag      420
ggccccttct ggcacggcgt cttccgggac ctgctcggcg acggcatctt caattccgac     480
ggcgacacct ggctcgcgca gcgcaagacg ccgcgctcg agttcaccac ccgcacgctc      540
cggacggcca tgtcccgctg ggtctcgcgc tccatccacg gccgcctcct gcccatcctg     600
gccgacgcgg ccaagggcaa ggcgcaggtg gatctccagg acctcctcct ccgcctcacc     660
ttcgacaaca tctgcggcct ggccttcggc aaggacccgg agacgctcgc ccagggcctg     720
ccggagaacg agttcgcctc cgcgttcgac cgcgccaccg aggccacgct caaccgcttc     780
atcttcccgg agttcctgtg gcgctgcaaa aagtggctgg gcctcggcat ggagaccacg      840
ctgaccagca gcatggccca cgtcgaccag tacctcgccg ccgtcatcaa gaagcgcaag      900
ctcgagctcg ccgccggcaa cggcaaatgc gacacggcgg cgacgcacga cgacctgctc      960
tcccggttca tgcggaaggg ttcctactcg gacgagtcgc tccagcacgt ggcgctcaac     1020
ttcatcctcg ccggccgcga cacctcctcc gtggcgctct cctggttctt ctggctcgtg    1080
```

```
tccacccacc ctgcggtgga gcgcaagatc gtgcgcgagc tctgctccgt tctcgccgcg    1140
tcacggggcg cccatgaccc ggcattgtgg ctggcggagc ccttcacctt cgaggagctc    1200
gaccgcctgg tctacctcaa ggcggcgctg tcggagaccc tccgcctcta ccctccgtc    1260 cccgaggact ccaagcacgt cgtcgcggac gactacctcc ccgacggcac cttcgtgccg    1320
gccgggtcgt cggtcaccta ctccatatac tcggcgggc gcatgaaggg ggtgtggggg    1380
gaggactgcc tcgagttccg gccggagcga tggctgtcgg ccgacggcac caagttcgag    1440
cagcacgact cgtacaagtt cgtggcgttc aacgccgggc cgagggtgtg cctgggcaag    1500
gacctagcct acctgcagat gaagaacatc gccgggagcg tgctgctccg gcaccgcctg    1560
accgtggcgc cgggccaccg cgtggagcag aagatgtcgc tcacgctctt catgaagggc    1620
gggctacgga tggaggtacg tccgcgcgac ctcgcccccg tcctcgacga gccctgcggc    1680
ctggacgccg gcgccgccac cgccgccgca gcaagtgcca cagcgccgtg cgcgtagaag    1740
acctggcacc ggcacgcgcc atgcatgatt cgtgcgtgct agctgttgaa gggacgccgg    1800
acattgaatg tgtagatagg gcagcagtgc aagaccgtaa gtaaaattga tgatgggttt    1860
ggtgacaaca ttgaagccac tccttttccag aatttacgac ccggatagga gaaacaggga    1920
aactttgcag atcacaacac aagatctagc cagccgggga tctgatctga tttgcgtctg    1980
ctcggagcac gggtgcatgg gagaccaagg aggaaaacaa aaaataacag aaacagagtg    2040
agcaatattt gtgattgtag ccacgggaaa gagagaggag taattagtaa ttcagatttg    2100
tttgcagtag ctcggtgttg gtgaccagat catagccaac taggctattc tattctattc    2160
tatttttgaa gatgattttt c                                              2181

<210> SEQ ID NO 11
<211> LENGTH: 39
<212> TYPE: DNA
<213> ORGANISM: Artificial Sequence
<220> FEATURE:
<223> OTHER INFORMATION: :

<400> SEQUENCE: 11
atatatggat ccatggaggt ggggacgtgg gcggtggtg                             39

<210> SEQ ID NO 12
<211> LENGTH: 150
<212> TYPE: DNA
<213> ORGANISM: Artificial Sequence
<220> FEATURE:
<223> OTHER INFORMATION: :

<400> SEQUENCE: 12
atatatggat ccatggaagt tggtacttgg gctgttgttg tttctgctgt tgctgcttat      60
atggcttggt tttggagaat gtctagaggt ttgagaggtc caagagtttg gccagttttg     120
ggttctttgc caggcctggt gcagcacgcc                                     150

<210> SEQ ID NO 13
<211> LENGTH: 42
<212> TYPE: DNA
<213> ORGANISM: Artificial Sequence
<220> FEATURE:
<223> OTHER INFORMATION: :

<400> SEQUENCE: 13
tatatagaat tccttctacg cgcacggcgc tgtggcactt gc                         42
```

<210> SEQ ID NO 14
<211> LENGTH: 1626
<212> TYPE: DNA
<213> ORGANISM: Artificial Sequence
<220> FEATURE:
<223> OTHER INFORMATION: :

<400> SEQUENCE: 14

| | | | | | |
|---|---|---|---|---|---|
| atggaagttg | gtacttgggc | tgttgttgtt | tctgctgttg | ctgcttatat | ggcttggttt | 60 |
| tggagaatgt | ctagaggttt | gagaggtcca | agagtttggc | cagttttggg | ttctttgcca | 120 |
| ggcctggtgc | agcacgccga | ggacatgcac | gagtggatcg | ccggcaacct | gcgccgcgcg | 180 |
| ggcggcacgt | accagacctg | catcttcgcc | gtgcccgggg | tggcgcgccg | cggcggcctg | 240 |
| gtcaccgtca | cctgcgaccc | cgcaacctg | agcacgtcc | tgaaggcgcg | cttcgacaac | 300 |
| taccccaagg | gccccttctg | gcacggcgtc | ttccgggacc | tgctcggcga | cggcatcttc | 360 |
| aattccgacg | gcgacacctg | gctcgcgcag | cgcaagacgg | ccgcgctcga | gttcaccacc | 420 |
| cgcacgctcc | ggacggccat | gtcccgctgg | gtctcgcgct | ccatccacgg | ccgcctcctg | 480 |
| cccatcctgg | ccgacgcggc | caagggcaag | gcgcaggtgg | atctccagga | cctcctcctc | 540 |
| cgcctcacct | tcgacaacat | ctgcggcctg | gccttcggca | aggacccgga | gacgctcgcc | 600 |
| cagggcctgc | cggagaacga | gttcgcctcc | gcgttcgacc | gcgccaccga | ggccacgctc | 660 |
| aaccgcttca | tcttcccgga | gttcctgtgg | cgctgcaaaa | agtggctggg | cctcggcatg | 720 |
| gagaccacgc | tgaccagcag | catggcccac | gtcgaccagt | acctcgccgc | cgtcatcaag | 780 |
| aagcgcaagc | tcgagctcgc | cgccggcaac | ggcaaatgcg | acacgcggc | gacgcacgac | 840 |
| gacctgctct | cccggttcat | gcggaagggt | tcctactcgg | acgagtcgct | ccagcacgtg | 900 |
| gcgctcaact | tcatcctcgc | cggccgcgac | acctcctccg | tggcgctctc | ctggttcttc | 960 |
| tggctcgtgt | ccacccaccc | tgcggtggag | cgcaagatcg | tgcgcgagct | ctgctccgtt | 1020 |
| ctcgccgcgt | cacggggcgc | ccatgacccg | gcattgtggc | tggcggagcc | cttcaccttc | 1080 |
| gaggagctcg | accgcctggt | ctacctcaag | gcggcgctgt | cggagaccct | ccgcctctac | 1140 |
| ccctccgtcc | ccgaggactc | caagcacgtc | gtcgcggacg | actacctccc | cgacggcacc | 1200 |
| ttcgtgccgg | ccgggtcgtc | ggtcacctac | tccatatact | cggcggggcg | catgaagggg | 1260 |
| gtgtgggggg | aggactgcct | cgagttccgg | ccggagcgat | ggctgtcggc | cgacggcacc | 1320 |
| aagttcgagc | agcacgactc | gtacaagttc | gtggcgttca | acgccgggcc | gagggtgtgc | 1380 |
| ctgggcaagg | acctagccta | cctgcagatg | aagaacatcg | ccgggagcgt | gctgctccgg | 1440 |
| caccgcctga | ccgtggcgcc | gggccaccgc | gtggagcaga | agatgtcgct | cacgctcttc | 1500 |
| atgaagggcg | ggctacggat | ggaggtacgt | ccgcgcgacc | tcgcccccgt | cctcgacgag | 1560 |
| ccctgcggcc | tggacgccgg | cgccgccacc | gccgccgcag | caagtgccac | agcgccgtgc | 1620 |
| gcgtag | | | | | | 1626 |

<210> SEQ ID NO 15
<211> LENGTH: 501
<212> TYPE: PRT
<213> ORGANISM: Artificial Sequence
<220> FEATURE:
<223> OTHER INFORMATION: :

<400> SEQUENCE: 15

Met Asp Val Leu Leu Leu Glu Lys Ala Leu Leu Gly Leu Phe Ala Ala
1               5                   10                  15

Ala Val Leu Ala Ile Ala Val Ala Lys Leu Thr Gly Lys Arg Phe Arg

```
              20                  25                  30
Leu Pro Pro Gly Pro Ser Gly Ala Pro Ile Val Gly Asn Trp Leu Gln
            35                  40                  45
Val Gly Asp Asp Leu Asn His Arg Asn Leu Met Gly Leu Ala Lys Arg
 50                  55                  60
Phe Gly Glu Val Phe Leu Arg Met Gly Val Arg Asn Leu Val Val
 65                  70                  75                  80
Val Ser Ser Pro Glu Leu Ala Lys Glu Val Leu His Thr Gln Gly Val
                85                  90                  95
Glu Phe Gly Ser Arg Thr Arg Asn Val Val Phe Asp Ile Phe Thr Gly
               100                 105                 110
Lys Gly Gln Asp Met Val Phe Thr Val Tyr Gly Asp His Trp Arg Lys
               115                 120                 125
Met Arg Arg Ile Met Thr Val Pro Phe Phe Thr Asn Lys Val Val Ala
               130                 135                 140
Gln Asn Arg Val Gly Trp Glu Glu Ala Arg Leu Val Val Glu Asp
145                 150                 155                 160
Leu Lys Ala Asp Pro Ala Ala Thr Ala Gly Val Val Arg Arg
               165                 170                 175
Arg Leu Gln Leu Met Met Tyr Asn Asp Met Phe Arg Ile Met Phe Asp
               180                 185                 190
Arg Arg Phe Glu Ser Val Ala Asp Pro Leu Phe Asn Gln Leu Lys Ala
               195                 200                 205
Leu Asn Ala Glu Arg Ser Ile Leu Ser Gln Ser Phe Asp Tyr Asn Tyr
               210                 215                 220
Gly Asp Phe Ile Pro Val Leu Arg Pro Phe Leu Arg Arg Tyr Leu Asn
225                 230                 235                 240
Arg Cys Thr Asn Leu Lys Thr Lys Arg Met Lys Val Phe Glu Asp His
                   245                 250                 255
Phe Val Gln Gln Arg Lys Glu Ala Leu Glu Lys Thr Gly Glu Ile Arg
               260                 265                 270
Cys Ala Met Asp His Ile Leu Glu Ala Glu Arg Lys Gly Glu Ile Asn
               275                 280                 285
His Asp Asn Val Leu Tyr Ile Val Glu Asn Ile Asn Val Ala Ala Ile
               290                 295                 300
Glu Thr Thr Leu Trp Ser Ile Glu Trp Gly Leu Ala Glu Leu Val Asn
305                 310                 315                 320
His Pro Glu Ile Gln Gln Lys Leu Arg Glu Glu Ile Val Ala Val Leu
               325                 330                 335
Gly Ala Gly Val Ala Val Thr Glu Pro Asp Leu Glu Arg Leu Pro Tyr
               340                 345                 350
Leu Gln Ser Val Val Lys Glu Thr Leu Arg Leu Arg Met Ala Ile Pro
               355                 360                 365
Leu Leu Val Pro His Met Asn Leu Ser Asp Ala Lys Leu Ala Gly Tyr
               370                 375                 380
Asp Ile Pro Ala Glu Ser Lys Ile Leu Val Asn Ala Trp Phe Leu Ala
385                 390                 395                 400
Asn Asp Pro Lys Arg Trp Val Arg Ala Asp Glu Phe Arg Pro Glu Arg
                   405                 410                 415
Phe Leu Glu Glu Glu Lys Ala Val Glu Ala His Gly Asn Asp Phe Arg
               420                 425                 430
Phe Val Pro Phe Gly Val Gly Arg Arg Ser Cys Pro Gly Ile Ile Leu
               435                 440                 445
```

-continued

```
Ala Leu Pro Ile Ile Gly Ile Thr Leu Gly Arg Leu Val Gln Asn Phe
    450                 455                 460
Gln Leu Pro Pro Pro Gly Gln Asp Lys Ile Asp Thr Thr Glu Lys
465                 470                 475                 480
Pro Gly Gln Phe Thr Asn Gln Ile Leu Lys His Ala Thr Ile Val Cys
                485                 490                 495
Lys Pro Leu Glu Ala
            500

<210> SEQ ID NO 16
<211> LENGTH: 501
<212> TYPE: PRT
<213> ORGANISM: Artificial Sequence
<220> FEATURE:
<223> OTHER INFORMATION: :

<400> SEQUENCE: 16

Met Asp Val Leu Leu Glu Lys Ala Leu Gly Leu Phe Ala Ala
  1               5                  10                  15
Ala Val Leu Ala Ile Ala Val Ala Lys Leu Thr Gly Lys Arg Phe Arg
                20                  25                  30
Leu Pro Pro Gly Pro Ser Gly Ala Pro Ile Val Gly Asn Trp Leu Gln
                35                  40                  45
Val Gly Asp Asp Leu Asn His Arg Asn Leu Met Gly Leu Ala Lys Arg
    50                  55                  60
Phe Gly Glu Val Phe Leu Leu Arg Met Gly Val Arg Asn Leu Val Val
65                  70                  75                  80
Val Ser Ser Pro Glu Leu Ala Lys Glu Val Leu His Thr Gln Gly Val
                85                  90                  95
Glu Phe Gly Ser Arg Thr Arg Asn Val Val Phe Asp Ile Phe Thr Gly
                100                 105                 110
Lys Gly Gln Asp Met Val Phe Thr Val Tyr Gly Asp His Trp Arg Lys
                115                 120                 125
Met Arg Arg Ile Met Thr Val Pro Phe Phe Thr Asn Lys Val Val Ala
    130                 135                 140
Gln Asn Arg Val Gly Trp Glu Glu Ala Arg Leu Val Val Glu Asp
145                 150                 155                 160
Leu Lys Ala Asp Pro Ala Ala Ala Thr Ala Gly Val Val Arg Arg
                165                 170                 175
Arg Leu Gln Leu Met Met Tyr Asn Asp Met Phe Arg Ile Met Phe Asp
                180                 185                 190
Arg Arg Phe Glu Ser Val Ala Asp Pro Leu Phe Asn Gln Leu Lys Ala
                195                 200                 205
Leu Asn Ala Glu Arg Ser Ile Leu Ser Gln Ser Phe Asp Tyr Asn Tyr
    210                 215                 220
Gly Asp Phe Ile Pro Val Leu Arg Pro Phe Leu Arg Arg Tyr Leu Asn
225                 230                 235                 240
Arg Cys Thr Asn Leu Lys Thr Lys Arg Met Lys Val Phe Glu Asp His
                245                 250                 255
Phe Val Gln Gln Arg Lys Glu Ala Leu Glu Lys Thr Gly Glu Ile Arg
                260                 265                 270
Cys Ala Met Asp His Ile Leu Glu Ala Glu Arg Lys Gly Glu Ile Asn
            275                 280                 285
His Asp Asn Val Leu Tyr Ile Val Glu Asn Ile Asn Val Ala Ala Ile
    290                 295                 300
```

```
Glu Thr Thr Leu Trp Ser Ile Glu Trp Gly Leu Ala Glu Leu Val Asn
305                 310                 315                 320

His Pro Glu Ile Gln Gln Lys Leu Arg Glu Ile Val Ala Val Leu
            325                 330                 335

Gly Ala Gly Val Ala Val Thr Glu Pro Asp Leu Glu Arg Leu Pro Tyr
                340                 345                 350

Leu Gln Ser Val Val Lys Glu Thr Leu Arg Leu Arg Met Ala Ile Pro
        355                 360                 365

Leu Leu Val Pro His Met Asn Leu Ser Asp Ala Lys Leu Ala Gly Tyr
    370                 375                 380

Asp Ile Pro Ala Glu Ser Lys Ile Leu Val Asn Ala Trp Phe Leu Ala
385                 390                 395                 400

Asn Asp Pro Lys Arg Trp Val Arg Ala Asp Glu Phe Arg Pro Glu Arg
                405                 410                 415

Phe Leu Glu Glu Glu Lys Ala Val Glu Ala His Gly Asn Asp Phe Arg
                420                 425                 430

Phe Val Pro Phe Gly Val Gly Arg Arg Ser Cys Pro Gly Ile Ile Leu
            435                 440                 445

Ala Leu Pro Ile Ile Gly Ile Thr Leu Gly Arg Leu Val Gln Asn Phe
    450                 455                 460

Gln Leu Leu Pro Pro Gly Gln Asp Lys Ile Asp Thr Thr Glu Lys
465                 470                 475                 480

Pro Gly Gln Phe Thr Asn Gln Ile Leu Lys His Ala Thr Ile Val Cys
                485                 490                 495

Lys Pro Leu Glu Ala
            500

<210> SEQ ID NO 17
<211> LENGTH: 501
<212> TYPE: PRT
<213> ORGANISM: Artificial Sequence
<220> FEATURE:
<223> OTHER INFORMATION: :

<400> SEQUENCE: 17

Met Asp Val Leu Leu Leu Glu Lys Ala Leu Leu Gly Leu Phe Ala Ala
1               5                   10                  15

Ala Val Leu Ala Ile Ala Val Ala Lys Leu Thr Gly Lys Arg Phe Arg
            20                  25                  30

Leu Pro Pro Gly Pro Ser Gly Ala Pro Ile Val Gly Asn Trp Leu Gln
        35                  40                  45

Val Gly Asp Asp Leu Asn His Arg Asn Leu Met Gly Leu Ala Lys Arg
    50                  55                  60

Phe Gly Glu Val Phe Leu Leu Arg Met Gly Val Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Asp His Trp Arg Lys
        115                 120                 125

Met Arg Arg Ile Met Thr Val Pro Phe Phe Thr Asn Lys Val Val Ala
    130                 135                 140

Gln Asn Arg Val Gly Trp Glu Glu Glu Ala Arg Leu Val Val Glu Asp
145                 150                 155                 160
```

```
Leu Lys Ala Asp Pro Ala Ala Thr Ala Gly Val Val Arg Arg
            165                 170                 175

Arg Leu Gln Leu Met Met Tyr Asn Asp Met Phe Arg Ile Met Phe Asp
                180                 185                 190

Arg Arg Phe Glu Ser Val Ala Asp Pro Leu Phe Asn Gln Leu Lys Ala
        195                 200                 205

Leu Asn Ala Glu Arg Ser Ile Leu Ser Gln Ser Phe Asp Tyr Asn Tyr
    210                 215                 220

Gly Asp Phe Ile Pro Val Leu Arg Pro Phe Leu Arg Arg Tyr Leu Asn
225                 230                 235                 240

Arg Cys Thr Asn Leu Lys Thr Lys Arg Met Lys Val Phe Glu Asp His
                245                 250                 255

Phe Val Gln Gln Arg Lys Glu Ala Leu Glu Lys Thr Gly Glu Ile Arg
                260                 265                 270

Cys Ala Met Asp His Ile Leu Glu Ala Glu Arg Lys Gly Glu Ile Asn
            275                 280                 285

His Asp Asn Val Leu Tyr Ile Val Glu Asn Ile Asn Val Ala Ala Ile
    290                 295                 300

Glu Thr Thr Leu Trp Ser Ile Glu Trp Gly Leu Ala Glu Leu Val Asn
305                 310                 315                 320

His Pro Glu Ile Gln Gln Lys Leu Arg Glu Glu Ile Val Ala Val Leu
                325                 330                 335

Gly Ala Gly Val Ala Val Thr Glu Pro Asp Leu Glu Arg Leu Pro Tyr
            340                 345                 350

Leu Gln Ser Val Val Lys Glu Thr Leu Arg Leu Arg Met Ala Ile Pro
        355                 360                 365

Leu Leu Val Pro His Met Asn Leu Ser Asp Ala Lys Leu Ala Gly Tyr
370                 375                 380

Asp Ile Pro Ala Glu Ser Lys Ile Leu Val Asn Ala Trp Phe Leu Ala
385                 390                 395                 400

Asn Asp Pro Lys Arg Trp Val Arg Ala Asp Glu Phe Arg Pro Glu Arg
                405                 410                 415

Phe Leu Glu Glu Glu Lys Ala Val Glu Ala His Gly Asn Asp Phe Arg
                420                 425                 430

Phe Val Pro Phe Gly Val Gly Arg Arg Ser Cys Pro Gly Ile Ile Leu
            435                 440                 445

Ala Leu Pro Ile Ile Gly Ile Thr Leu Gly Arg Leu Val Gln Asn Phe
450                 455                 460

Gln Leu Leu Pro Pro Gly Gln Asp Lys Ile Asp Thr Thr Glu Lys
465                 470                 475                 480

Pro Gly Gln Phe Thr Asn Gln Ile Leu Lys His Ala Thr Ile Val Cys
                485                 490                 495

Lys Pro Leu Glu Ala
            500
```

<210> SEQ ID NO 18
<211> LENGTH: 501
<212> TYPE: PRT
<213> ORGANISM: Artificial Sequence
<220> FEATURE:
<223> OTHER INFORMATION: :

<400> SEQUENCE: 18

```
Met Asp Val Leu Leu Leu Glu Lys Ala Leu Leu Gly Leu Phe Ala Ala
1               5                   10                  15
```

-continued

```
Ala Val Leu Ala Ile Ala Val Ala Lys Leu Thr Gly Lys Arg Phe Arg
             20                  25                  30

Leu Pro Pro Gly Pro Ser Gly Ala Pro Ile Val Gly Asn Trp Leu Gln
             35                  40                  45

Val Gly Asp Asp Leu Asn His Arg Asn Leu Met Gly Leu Ala Lys Arg
 50                      55                  60

Phe Gly Glu Val Phe Leu Leu Arg Met Gly Val Arg Asn Leu Val Val
 65                  70                  75                  80

Val Ser Ser Pro Glu Leu Ala Lys Glu Val Leu His Thr Gln Gly Val
                 85                  90                  95

Glu Phe Gly Ser Arg Thr Arg Asn Val Val Phe Asp Ile Phe Thr Gly
                100                 105                 110

Lys Gly Gln Asp Met Val Phe Thr Val Tyr Gly Asp His Trp Arg Lys
            115                 120                 125

Met Arg Arg Ile Met Thr Val Pro Phe Phe Thr Asn Lys Val Val Ala
        130                 135                 140

Gln Asn Arg Val Gly Trp Glu Glu Ala Arg Leu Val Val Glu Asp
145                 150                 155                 160

Leu Lys Ala Asp Pro Ala Ala Thr Ala Gly Val Val Arg Arg
                165                 170                 175

Arg Leu Gln Leu Met Met Tyr Asn Asp Met Phe Arg Ile Met Phe Asp
            180                 185                 190

Arg Arg Phe Glu Ser Val Ala Asp Pro Leu Phe Asn Gln Leu Lys Ala
                195                 200                 205

Leu Asn Ala Glu Arg Ser Ile Leu Ser Gln Ser Phe Asp Tyr Asn Tyr
        210                 215                 220

Gly Asp Phe Ile Pro Val Leu Arg Pro Phe Leu Arg Arg Tyr Leu Asn
225                 230                 235                 240

Arg Cys Thr Asn Leu Lys Thr Lys Arg Met Lys Val Phe Glu Asp His
                245                 250                 255

Phe Val Gln Gln Arg Lys Glu Ala Leu Glu Lys Thr Gly Glu Ile Arg
                260                 265                 270

Cys Ala Met Asp His Ile Leu Glu Ala Glu Arg Lys Gly Glu Ile Asn
            275                 280                 285

His Asp Asn Val Leu Tyr Ile Val Glu Asn Ile Asn Val Ala Ala Ile
        290                 295                 300

Glu Thr Thr Leu Trp Ser Ile Glu Trp Gly Leu Ala Glu Leu Val Asn
305                 310                 315                 320

His Pro Glu Ile Gln Gln Lys Leu Arg Glu Glu Ile Val Ala Val Leu
                325                 330                 335

Gly Ala Gly Val Ala Val Thr Glu Pro Asp Leu Glu Arg Leu Pro Tyr
            340                 345                 350

Leu Gln Ser Val Val Lys Glu Thr Leu Arg Leu Arg Met Ala Ile Pro
        355                 360                 365

Leu Leu Val Pro His Met Asn Leu Ser Asp Ala Lys Leu Ala Gly Tyr
    370                 375                 380

Asp Ile Pro Ala Glu Ser Lys Ile Leu Val Asn Ala Trp Phe Leu Ala
385                 390                 395                 400

Asn Asp Pro Lys Arg Trp Val Arg Ala Asp Glu Phe Arg Pro Glu Arg
                405                 410                 415

Phe Leu Glu Glu Glu Lys Ala Val Glu Ala His Gly Asn Asp Phe Arg
                420                 425                 430
```

```
Phe Val Pro Phe Gly Val Gly Arg Arg Ser Cys Pro Gly Ile Ile Leu
        435                 440                 445

Ala Leu Pro Ile Ile Gly Ile Thr Leu Gly Arg Leu Val Gln Asn Phe
    450                 455                 460

Gln Leu Leu Pro Pro Gly Gln Asp Lys Ile Asp Thr Thr Glu Lys
465                 470                 475                 480

Pro Gly Gln Phe Thr Asn Gln Ile Leu Lys His Ala Thr Ile Val Cys
                485                 490                 495

Lys Pro Leu Glu Ala
            500

<210> SEQ ID NO 19
<211> LENGTH: 541
<212> TYPE: PRT
<213> ORGANISM: Artificial Sequence
<220> FEATURE:
<223> OTHER INFORMATION: :

<400> SEQUENCE: 19

Met Glu Val Gly Thr Trp Ala Val Val Ser Ala Val Ala Ala Tyr
1               5                   10                  15

Met Ala Trp Phe Trp Arg Met Ser Arg Gly Leu Arg Gly Pro Arg Val
            20                  25                  30

Trp Pro Val Leu Gly Ser Leu Pro Gly Leu Val Gln His Ala Glu Asp
        35                  40                  45

Met His Glu Trp Ile Ala Gly Asn Leu Arg Arg Ala Gly Gly Thr Tyr
    50                  55                  60

Gln Thr Cys Ile Phe Ala Val Pro Gly Val Ala Arg Arg Gly Gly Leu
65                  70                  75                  80

Val Thr Val Thr Cys Asp Pro Arg Asn Leu Glu His Val Leu Lys Ala
                85                  90                  95

Arg Phe Asp Asn Tyr Pro Lys Gly Pro Phe Trp His Gly Val Phe Arg
            100                 105                 110

Asp Leu Leu Gly Asp Gly Ile Phe Asn Ser Asp Gly Asp Thr Trp Leu
        115                 120                 125

Ala Gln Arg Lys Thr Ala Ala Leu Glu Phe Thr Thr Arg Thr Leu Arg
    130                 135                 140

Thr Ala Met Ser Arg Trp Val Ser Arg Ser Ile His Gly Arg Leu Leu
145                 150                 155                 160

Pro Ile Leu Ala Asp Ala Ala Lys Gly Lys Ala Gln Val Asp Leu Gln
                165                 170                 175

Asp Leu Leu Arg Leu Thr Phe Asp Asn Ile Cys Gly Leu Ala Phe
            180                 185                 190

Gly Lys Asp Pro Glu Thr Leu Ala Gln Gly Leu Pro Glu Asn Glu Phe
        195                 200                 205

Ala Ser Ala Phe Asp Arg Ala Thr Glu Ala Thr Leu Asn Arg Phe Ile
    210                 215                 220

Phe Pro Glu Phe Leu Trp Arg Cys Lys Lys Trp Leu Gly Leu Gly Met
225                 230                 235                 240

Glu Thr Thr Leu Thr Ser Ser Met Ala His Val Asp Gln Tyr Leu Ala
                245                 250                 255

Ala Val Ile Lys Lys Arg Lys Leu Glu Leu Ala Ala Gly Asn Gly Lys
            260                 265                 270

Cys Asp Thr Ala Ala Thr His Asp Asp Leu Leu Ser Arg Phe Met Arg
        275                 280                 285
```

```
Lys Gly Ser Tyr Ser Asp Glu Ser Leu Gln His Val Ala Leu Asn Phe
    290             295             300
Ile Leu Ala Gly Arg Asp Thr Ser Ser Val Ala Leu Ser Trp Phe Phe
305             310             315             320
Trp Leu Val Ser Thr His Pro Ala Val Glu Arg Lys Ile Val Arg Glu
                325             330             335
Leu Cys Ser Val Leu Ala Ala Ser Arg Gly Ala His Asp Pro Ala Leu
            340             345             350
Trp Leu Ala Glu Pro Phe Thr Phe Glu Glu Leu Asp Arg Leu Val Tyr
        355             360             365
Leu Lys Ala Ala Leu Ser Glu Thr Leu Arg Leu Tyr Pro Ser Val Pro
    370             375             380
Glu Asp Ser Lys His Val Val Ala Asp Tyr Leu Pro Asp Gly Thr
385             390             395             400
Phe Val Pro Ala Gly Ser Ser Val Thr Tyr Ser Ile Tyr Ser Ala Gly
                405             410             415
Arg Met Lys Gly Val Trp Gly Glu Asp Cys Leu Glu Phe Arg Pro Glu
            420             425             430
Arg Trp Leu Ser Ala Asp Gly Thr Lys Phe Glu Gln His Asp Ser Tyr
        435             440             445
Lys Phe Val Ala Phe Asn Ala Gly Pro Arg Val Cys Leu Gly Lys Asp
    450             455             460
Leu Ala Tyr Leu Gln Met Lys Asn Ile Ala Gly Ser Val Leu Leu Arg
465             470             475             480
His Arg Leu Thr Val Ala Pro Gly His Arg Val Glu Gln Lys Met Ser
                485             490             495
Leu Thr Leu Phe Met Lys Gly Gly Leu Arg Met Glu Val Arg Pro Arg
            500             505             510
Asp Leu Ala Pro Val Leu Asp Glu Pro Cys Gly Leu Asp Ala Gly Ala
        515             520             525
Ala Thr Ala Ala Ala Ala Ser Ala Thr Ala Pro Cys Ala
    530             535             540

<210> SEQ ID NO 20
<211> LENGTH: 541
<212> TYPE: PRT
<213> ORGANISM: Artificial Sequence
<220> FEATURE:
<223> OTHER INFORMATION: :

<400> SEQUENCE: 20

Met Glu Val Gly Thr Trp Ala Val Val Ser Ala Val Ala Ala Tyr
1               5               10              15
Met Ala Trp Phe Trp Arg Met Ser Arg Gly Leu Arg Gly Pro Arg Val
            20              25              30
Trp Pro Val Leu Gly Ser Leu Pro Gly Leu Val Gln His Ala Glu Asp
        35              40              45
Met His Glu Trp Ile Ala Gly Asn Leu Arg Arg Ala Gly Gly Thr Tyr
    50              55              60
Gln Thr Cys Ile Phe Ala Val Pro Gly Val Ala Arg Arg Gly Gly Leu
65              70              75              80
Val Thr Val Thr Cys Asp Pro Arg Asn Leu Glu His Val Leu Lys Ala
                85              90              95
Arg Phe Asp Asn Tyr Pro Lys Gly Pro Phe Trp His Gly Val Phe Arg
            100             105             110
```

-continued

```
Asp Leu Leu Gly Asp Gly Ile Phe Asn Ser Asp Gly Asp Thr Trp Leu
        115                 120                 125

Ala Gln Arg Lys Thr Ala Ala Leu Glu Phe Thr Thr Arg Thr Leu Arg
    130                 135                 140

Thr Ala Met Ser Arg Trp Val Ser Arg Ser Ile His Gly Arg Leu Leu
145                 150                 155                 160

Pro Ile Leu Ala Asp Ala Ala Lys Gly Lys Ala Gln Val Asp Leu Gln
                165                 170                 175

Asp Leu Leu Arg Leu Thr Phe Asp Asn Ile Cys Gly Leu Ala Phe
            180                 185                 190

Gly Lys Asp Pro Glu Thr Leu Ala Gln Gly Leu Pro Glu Asn Glu Phe
        195                 200                 205

Ala Ser Ala Phe Asp Arg Ala Thr Glu Ala Thr Leu Asn Arg Phe Ile
    210                 215                 220

Phe Pro Glu Phe Leu Trp Arg Cys Lys Lys Trp Leu Gly Leu Gly Met
225                 230                 235                 240

Glu Thr Thr Leu Thr Ser Ser Met Ala His Val Asp Gln Tyr Leu Ala
                245                 250                 255

Ala Val Ile Lys Lys Arg Lys Leu Glu Leu Ala Ala Gly Asn Gly Lys
            260                 265                 270

Cys Asp Thr Ala Ala Thr His Asp Asp Leu Leu Ser Arg Phe Met Arg
        275                 280                 285

Lys Gly Ser Tyr Ser Asp Glu Ser Leu Gln His Val Ala Leu Asn Phe
    290                 295                 300

Ile Leu Ala Gly Arg Asp Thr Ser Ser Val Ala Leu Ser Trp Phe Phe
305                 310                 315                 320

Trp Leu Val Ser Thr His Pro Ala Val Glu Arg Lys Ile Val Arg Glu
                325                 330                 335

Leu Cys Ser Val Leu Ala Ala Ser Arg Gly Ala His Asp Pro Ala Leu
            340                 345                 350

Trp Leu Ala Glu Pro Phe Thr Phe Glu Glu Leu Asp Arg Leu Val Tyr
        355                 360                 365

Leu Lys Ala Ala Leu Ser Glu Thr Leu Arg Leu Tyr Pro Ser Val Pro
    370                 375                 380

Glu Asp Ser Lys His Val Val Ala Asp Tyr Leu Pro Asp Gly Thr
385                 390                 395                 400

Phe Val Pro Ala Gly Ser Ser Val Thr Tyr Ser Ile Tyr Ser Ala Gly
                405                 410                 415

Arg Met Lys Gly Val Trp Gly Glu Asp Cys Leu Glu Phe Arg Pro Glu
            420                 425                 430

Arg Trp Leu Ser Ala Asp Gly Thr Lys Phe Glu Gln His Asp Ser Tyr
        435                 440                 445

Lys Phe Val Ala Phe Asn Ala Gly Pro Arg Val Cys Leu Gly Lys Asp
    450                 455                 460

Leu Ala Tyr Leu Gln Met Lys Asn Ile Ala Gly Ser Val Leu Leu Arg
465                 470                 475                 480

His Arg Leu Thr Val Ala Pro Gly His Arg Val Glu Gln Lys Met Ser
                485                 490                 495
```

```
Leu Thr Leu Phe Met Lys Gly Gly Leu Arg Met Glu Val Arg Pro Arg
            500                 505                 510

Asp Leu Ala Pro Val Leu Asp Glu Pro Cys Gly Leu Asp Ala Gly Ala
        515                 520                 525

Ala Thr Ala Ala Ala Ala Ser Ala Thr Ala Pro Cys Ala
    530                 535             540
```

RECORDING OF DNA SEQUENCES TO ENABLE THEM TO BE EXPRESSED IN YEASTS, AND THE TRANSFORMED YEASTS OBTAINED

This application is continuation of U.S. patent application Ser. No. 09/158,767, filed Sep. 23, 1998, now U.S. Pat. No. 6,180,363, issued Jan. 30, 2001.

The present invention relates to the recoding of DNA sequences which encode proteins which contain regions having a high content of codons which are poorly translated by yeasts, in particular which encode proteins of plant origin, such as the P450 cytochromes of plant origin, and to their expression in yeasts.

It is known that certain sequences encoding proteins of interest, in particular proteins of plant origin, are not readily translated in yeasts. This applies, in particular, to proteins which possess regions having a high content of codons which are poorly suited to yeasts, in particular leucine codons, such as some P450 cytochromes of plant origin. Some systems which have been developed for improving the expression of P450 cytochromes of animal or plant origin in yeasts, such as those described by Pompon et al. (*Methods Enzymol.*, 272, 1996, 51–64; WO 97/10344), have turned out to be unsuitable for large numbers of P450 cytochromes which encompass regions having a high content of codons which are poorly suited to yeasts.

The P450 cytochromes constitute a superfamily of membrane enzymes of the monooxygenase type which are able to oxidize a large family of generally hydrophobic substrates. The reactions are most frequently characterized by the oxidation of C—H or C=C bonds, and of heteroatoms, and, more rarely, by the reduction of nitro groups or by dehalogenation. More specifically, these enzymes are involved in the metabolism of xenobiotic substances and drugs and in the biosynthesis of secondary metabolites in plants, some of which have organoleptic or pharmacodynamic properties.

As a consequence, the P450 cytochromes are used, in particular, in:
- the in vitro diagnosis of the formation of toxic or mutagenic metabolites (molecules of natural origin, pollutants, drugs, pesticides, etc.), making it possible, in particular, to develop novel active molecules (pharmaceutical, agrochemistry),
- the identification and destruction of molecules which are toxic for, or pollute, the environment,
- the enzymic synthesis of novel molecules.

The search for heterologous expression of P450 cytochromes by host cells, more specifically yeasts, is therefore important for obtaining controlled production of this enzyme in large quantity, either for isolating it and using it in the above-listed processes, or for using the transformed cells directly for the said processes without previously isolating the enzyme.

The present invention provides a solution to the above-mentioned problem, enabling proteins which contain regions having a high content of codons which are poorly suited to yeasts, in particular P450 cytochromes of plant origin, to be expressed in yeasts.

The present invention therefore relates to a DNA sequence, in particular a cDNA sequence, which encodes a protein of interest which contains regions having a high content of codons which are poorly suited to yeasts, characterized in that a sufficient number of codons which are poorly suited to yeasts is replaced with corresponding codons which are well-suited to yeasts in the said regions having a high content of codons which are poorly suited to yeasts.

Within the meaning of the present invention, "codons which are poorly suited to yeasts" are understood as being codons whose frequency of use by yeasts is less than or equal to approximately 13 per 1000, preferably less than or equal to approximately 12 per 1000, more preferably less than or equal to approximately 10 per 1000. The frequency at which codons are used by yeasts, more specifically by *S. cerevisiae*, is described, in particular, in "Codon usage database" by Yasukazu Nakamura (available on the Kazusa world wide web server). This applies, in particular, to codons CTC, CTG and CTT, which encode leucine, to codons CGG, CGC, CGA, CGT and AGG, which encode arginine, to codons GCG and GCC, which encode alanine, to codons GGG, GGC and GGA, which encode glycine, and to codons CCG and CCC, which encode proline. The codons which are poorly suited to yeasts in accordance with the invention are, more specifically, codons CTC and CTG, which encode leucine, CGG, CGC, CGA, CGT and AGG, which encode arginine, codons GCG and GCC, which encode alanine, GGG and GGC, which encode glycine, and codons CCG and CCC, which encode proline.

Within the meaning of the present invention, "corresponding codons which are well-suited to yeasts" are understood as being the codons which correspond to the codons which are poorly suited to yeasts and which encode the same amino acids, and whose frequency of use by yeasts is greater than 15 per 1000, preferably greater than or equal to 18 per 1000, more preferably greater than or equal to 20 per 1000. This applies, in particular, to codons TTG and TTA, preferably TTG, which encode leucine, to codon AGA, which encodes arginine, to codons GCT and GCA, preferably GCT, which encode alanine, to codon GGT, which encodes glycine, and to codon CCA, which encodes proline.

Within the meaning of the present invention, "region having a high content of codons which are poorly suited to yeasts" is understood as being any region of the DNA sequence which contains at least 2 poorly suited codons among 10 consecutive codons, with it being possible for the two codons to be adjacent or separated by up to B other codons. According to one preferred embodiment of the invention, the regions having a high content of poorly suited codons contain 2, 3, 4, 5 or 6 poorly suited codons per 10 consecutive codons, or contain at least 2 or 3 adjacent poorly suited codons.

Within the meaning of the present invention, "sufficient number of codons" is understood as being the number of codons which it is necessary and sufficient to replace in order to observe a substantial improvement in their expression in yeasts. Advantageously, at least 50% of the codons which are poorly suited to yeasts in the high-content region under consideration are replaced with well-suited codons. Preferably, at least 75% of the poorly suited codons of the said region are replaced, with 100% of the poorly suited codons more preferably being replaced.

Within the meaning of the present invention, "substantial improvement" is understood as being either a detectable expression when no expression of the reference sequence is observed, or an increase in expression as compared with the level at which the reference sequence is expressed.

Within the meaning of the present invention, "reference sequence" designates any sequence which encodes a protein of interest and which is modified in accordance with the invention in order to promote its expression in yeasts.

The present invention is particularly well suited to DNA sequences, in particular cDNA sequences, which encode proteins of interest which contain regions having a high content of leucine and in which a sufficient number of CTC codons encoding leucine in the said region having a high content of leucine is replaced with TTG and/or TTA codons, or in which a sufficient number of CTC and CTG codons encoding leucine in the said region having a high content of leucine is replaced with TTG and/or TTA codons, preferably with a TTG codon.

Within the meaning of the present invention, "region having a high content of leucine" is understood w as being a region which contains at least 2 leucines among 10 consecutive amino acids in the protein of interest, with it being possible for the two leucines to be adjacent or separated by up to 8 other amino acids. According to one preferred embodiment of the invention, the regions having a high content of leucine contain 2, 3, 4, 5 or 6 leucines per 10 consecutive amino acids, or contain at least 2 or 3 adjacent leucines.

According to a preferred embodiment of the invention, at least 50% of the CTC or CTC and CTG codons of the region having a high content of leucine are replaced with TTG or TTA codons, with at least 75% of the CTC or CTC and CTG codons of the said region preferably being replaced, and 100% of the CTC or CTC and CTG codons more preferably being replaced.

Advantageously, the present invention is particularly suitable for DNA sequences whose general content of poorly suited codons is at least 20%, more preferably at least 30%, as compared with the total number of codons in the reference sequence.

Advantageously, when the reference sequence contains at least one 5 ' region having a high content of poorly suited codons, the recoding of this 5' region alone makes it possible to obtain a substantial improvement in the expression of the protein of interest in yeasts. The length of the 5' region to be recoded in accordance with the invention will vary depending on the length of the region having a high content of poorly suited codons. This length will advantageously be at least four codons, in particular when this region contains at least two adjacent poor codons, up to approximately 40 codons or more.

However, it is not necessary, according to the invention, to recode all the reference sequence, but only the regions having a high content of poor codons, in particular the 5' region on its own, in order to obtain a substantial improvement in the expression of the protein of interest in yeasts.

Advantageously, the DNA sequence encoding a protein of interest is an isolated DNA sequence of natural origin, in particular of plant origin. The invention is particularly advantageous for sequences which originate from monocotyledonous or dicotyledonous plants, preferably monocotyledonous plants, in particular of the graminae family, such as wheat, barley, oats, rice, maize, sorghum, cane sugar, etc.

According to a preferred embodiment of the invention, the DNA sequence encodes an enzyme, in particular a cytochrome P450, which is preferably of plant origin. These P450 cytochromes exhibit a high content of poorly suited codons, in particular encoding leucine, in their N-terminal region; it is in the 5' terminal coding region that the poorly suited codons are replaced.

The present invention also relates to a chimeric gene which comprises a DNA sequence which has been modified as above and heterologous 5' and 3'0 regulatory elements which are able to function in a yeast, that is to say which are able to control the expression of the protein of interest in the yeast. Such regulatory elements are well known to the skilled person and are described, in particular, by Rozman et al. (Genomics, 38, 1996, 371–381) and by Nacken et al. (Gene, 175, 1996, 253–260, *Probing the limits of expression levels by varying promoter strength and plasmid copy number in Saccharomyces cerevisiae*).

The present invention also relates to a vector for transforming yeasts which contains at least one chimeric gene as described above. It also relates to a process for transforming yeasts with the said vector and to the transformed yeasts which are obtained. It finally relates to a process for producing a heterologous protein of interest in a transformed yeast, with the sequence which encodes the said protein of interest being such as defined above.

The process for producing a heterologous protein of interest in a transformed yeast comprises the steps of:

a) transforming a yeast with a vector which is able to replicate in yeasts and which contains a modified DNA sequence as defined above and heterologous 5' and 3' regulatory elements which are able to function in a yeast, b) culturing the transformed yeast, and c) extracting the protein of interest from the yeast culture.

When the protein of interest is an enzyme which is suitable for transforming a substrate, such as a cytochrome P450, the enzyme which has been extracted from the yeast culture is then used for catalysing the transformation of the said substrate.

However, the catalysis can be carried out, without requiring the extraction of the yeast, by culturing the transformed yeast in the presence of the said substrate.

The present invention also relates, therefore, to a process for transforming a substrate by enzymic catalysis using an enzyme which is expressed in a yeast, which process comprises the steps of a) culturing the yeast which has been transformed in accordance with the invention in the presence of the substrate to be transformed, then b) recovering the transformed substrate from the yeast culture.

When the yeast has been transformed for expressing a cytochrome P450, the reaction which is catalysed by the enzyme is an oxidation reaction, more specifically a reaction in which C—H or C=C bonds are oxidized.

The techniques for transforming and culturing yeasts are known to the skilled person, and are described, for example, in *Methods in Enzymology* (Vol. 194, 1991).

Yeasts which are of use in accordance with the invention are selected, in particular, from the genera Saccharomyces, Kluyveromyces, Hansenula, Pichia and Yarrowia. Advantageously, the yeast belongs to the Saccaromyces genus, and is in particular *S. cerevisiae.*

Other characteristics of the invention will become apparent in the light of the examples which follow.

EXAMPLE 1

Production of a Wheat CDNA Gene Library, and Identification of the CYP73A17 Sequence The wheat cytochrome P450 CYP73A17 sequence was obtained by screening a young wheat plantlet (shoots and roots without the caryopses) cDNA library which was constructed in the vector λ-ZapII (Stratagene) in accordance with the supplier's instructions.

1. Production of the CDNA Library

*Triticum aestivum* (L. cv. Darius) seeds which had been coated with cloquintocet-mexyl (0.1% per dry weight of seed) are cultured in plastic boxes on two layers of damp gauze until shoots having a size of 3 to 5 mm are obtained. The water in the boxes is then replaced with a solution of 4 mM sodium phenobarbital and the wheat is cultured until the shoots are approximately 1 cm in size.

The cDNA library is constructed in the λ-ZapII (Stratagene) vector, in accordance with the supplier's protocol and instructions, using 5 μg of poly(A)$^{30}$ RNA (Lesot, A., Benveniste, I., Hasenfratz, M. P., Durst, F. (1990) Induction of NADPH cytochrome P450(c) reductase in wounded tissues from *Helianthus tuberosus* tubers. Plant Cell Physiol., 31, 1177–1182) which were isolated from the treated roots and shoots.

2. Screening the CDNA Library

5×10$^5$ lysis plaques from the previously obtained λ-ZapII library are screened using a probe which corresponds to the complete coding sequence of *Helianthus tuberosus* CYP73A1, and which has been labelled by random priming with [α-$^{32}$P]dCTP. The filters are prehybridized and hybridized at low stringency at 55° C. in accordance with the standard protocols. The membranes are washed twice for 10 minutes with 2×SSC, 0.1% SDS, and once for 10 minutes with 0.2×SSC, 0.1% SDS at ambient temperature, then twice for 30 minutes with 0.2×SSC, 0.1% SDS at 45° C. The inserts of the positive lysis plaques are analysed by PCR (polymerization chain reaction) and hybridization in order to determine their size. The clones containing inserts which hybridize with CYP73A1 under the above-described conditions and which are greater than 1.5 kbp in size are rescreened before excision of the pBluescript plasmid in accordance with the supplier's (Stratagene) protocol and sequencing using the Ready Reaction Dye Deoxy Terminator Cycle prism technique developed by Applied Biosystems Inc. A full length clone is then identified by alignment with CYP73A1.

The wheat cytochrome P450 CYP73Al7 which is encoded by the isolated sequence of SEQ ID NO: 1(which encodes the amino acid sequence of SEQ ID NO: 15) exhibits 76.2% identity with the *Helianthus tuberosus* CYP73A1.

EXAMPLE 2

Alterations to the Sequence Encoding the Wheat Cytochrome P450 CYP73A17

Contrary to the situation with regard to *Helianthus tuberosus* CYP73A1, which can be expressed in yeasts (Urban et al., 1994), repeated attempts to express wheat CYP73A17 in yeasts using the same customary techniques proved to be fruitless when the nucleotide sequence was not altered at the time it was inserted into the expression vector (verification by sequencing). No protein is detected by spectrophotometry or by immunoblotting, just as no enzymic activity is detectable in the microsomes of transformed and induced yeast.

1. Alteration of the Coding Sequence

The sequence encoding wheat CYP73A17 (SEQ. ID No. 1) was therefore altered, in three different ways, by PCR-induced mutagenesis, as follows:

The BamHI and EcoRI restriction sites were respectively introduced by PCR just upstream of the ATG codon and just downstream of the stop codon of the CYP73A17 coding sequence (source, origin) using the sense and reverse primers described below, with the restriction sites being BamHI in the case of the sense primers Rec1 (SEQ ID No. 3), Rec2 (SEQ ID No. 4) and 3(SEQ ID No. 5), and EcoRI in the case of the reverse primer (SEQ ID No. 6).

A primer, represented by SEQ ID No. 2, was also employed for enabling yeasts to be transformed with the unmodified (native) sequence encoding wheat CYP73A17.

The five primers described above were obtained from Eurogentech, and were synthesized and purified in accordance with customary methods.

For each alteration using the four different sense primers, the mode of operation is as follows:

The reaction mixture (20 mM Tris-HCl, pH 8.75, 10 mM KCl, 10 mM (NH$_4$)$_2$SO$_4$, 2 mM MgSO$_4$, 0.1% Triton X100, 0.1 mg/ml BSA, 5% (v/v) DMSO, 300 μM dNTP, 20 pmoles of each primer, 150 ng of template, total volume 50 μl) is preheated at 94° C. for 2 minutes before adding 5 units of Pfu DNA polymerase (Stratagene). After 2 minutes at 94° C., 30 amplification cycles are carried out as follows: 1 minute of denaturation at 94° C., 2 minutes of hybridization at 55° C., 2 minutes of extension at 72° C. The reaction is completed by 10 minutes of extension at 72° C.

For each primer, a sequence is obtained which is derived from sequence ID No. 1, and which is represented, in the case of the altered coding sequences, by the sequences ID No. 7 which encodes the amino acid sequence of SEQ. ID NO: 16), No. 8 which encodes the amino acid sequence of SEQ. ID NO: 17) and No. 9 which encodes the amino acid sequence of SEQ. ID NO: 18). The 5' ends of the sequences obtain using the four abovementioned sense primers are depicted below, with the BamHI restriction site being shown in italics:

```
native:  ATATAT*GGATCC* ATG GAC GTC CTC CTC CTG GAG AAG GCC

Rec 1    ATATAT*GGATCC* ATG GAT GTT TTG TTG TTG GAG AAG GCC

Rec 2    ATATAT*GGATCC* ATG GAT GTT TTG TTG TTG GAA AAA GCT

Rec 3    ATATAT*GGATCC* ATG GAT GTT TTG TTG TTG GAA AAA GCT

Protein:                met asp val leu leu leu glu lys ala

CTC CTG GGC CTC TTC GCC GCG GCG GTG CTG GCC ATC GCC GTC GCC

CTC CTG GGC CTC TTC GCC GCG GCG GTG CTG GCC ATC GCC GTC GCC

TTG TTG GGT TTG TTC GCC GCG GCG GTG CTG GCC ATC GCC GTC GCC

TTG TTG GGT TTG TTT GCT GCT GCT GTT TTG GCT ATT GCT GTT GCT
```

-continued

```
leu leu gly leu phe ala ala ala val leu ala ile ala val ala

AAG CTC ACC GGC AAG CGC TTC CGC CTC CCC CCT GGC CCC TCC GGC

AAG CTC ACC GGC AAG CGC TTC CGC CTC CCC CCT GGC CCC TCC GGC

AAG CTC ACC GGC AAG CGC TTC CGC CTC CCC CCT GGC CCC TCC GGC

AAA TTG ACT GGT AAA AGA TTT AGA TTG CCA CCA GGT CCA TCC GGC lys leu thr gly lys arg phe arg leu pro pro gly pro ser gly

GCC CCC ATC GTC .....

GCC CCC ATC GTC .....

GCC CCC ATC GTC .....

GCC CCC ATC GTC .....

ala pro ile val .....
```

2. Transforming the Yeasts

After having been digested with the restriction enzymes BamHI and EcoRI, the four above-described altered coding sequences are integrated into the vector pYeDP60, which is described by Pompon et al. (*Methods Enzymol*, 272, 1996, 51–64; WO 97/10344), the content of which is hereby incorporated by reference with regard to the plasmid, the method of insertion into the plasmid, and the method of transforming and growing the yeasts, in particular using the *Saccharomyces cerevisiae* yeast strains W(R), WAT21 and WAT11. The method for transforming and growing yeasts is also described by Pompon et al. and by Urban et al. (*Eur. J. Biochem*, 222, 1994, page 844, 2nd column, "Yeast transformation and cell culture").

4 transformed yeast strains, designated: W73A17(native), W73A17(Rec1), W73A17(Rec2) and W73A17(Rec3), are obtained.

EXAMPLE 3

Expression of CYP73A17 in the Altered Yeasts

The previously obtained transformed yeasts are cultured, in accordance with the method described by Urban et al. (*Eur. J. Biochem.*, 222, 1994, page 844, 2nd column, "Yeast transformation and cell culture"), in 50 ml of SGI medium at 30° C. for 72 h. The cells are recovered by centrifuging at 8000 g for 10 minutes, washed with 25 ml of YPI medium, recentrifuged, and then resuspended in 250 ml of YPI medium. The cells are induced with galactose for 14–16 h, while being shaken at 160 rpm, until the cell density reaches $10^8$ cells per ml. The microsomes are then prepared using the method described by Pierrel et al. (*Eur. J. Biochem.*, 224, 1994, 835–844).

The expression of CYP73A17 achieved in the case of the four strains is quantified by differential spectrophotometry using the method described by Omura and Sato (*J. Biol. Chem.*, 177, 678–693). It is proportional to the number of poorly suited codons which have been altered.

The microsomal enzymic activity is measured using the method described by Durst F., Benveniste I., Schalk M. and Werck-Reichhart D. (1996) Cinnamic acid hydroxylase activity in plant microsomes. Methods Enzymol. 272, 259–268. The results obtained after transforming WAT21 are recorded in the Table below. The activity is expressed as cinnamate 4-hydroxylase activity. The percentage additional activity (rounded values) illustrates the extent of the leap in activity which is observed after the poorly suited codons have been altered.

| Strain | Activity pmol/min/µg of protein | % additional activity |
|---|---|---|
| W73A17 native | 0.64 | — |
| W73A17 Rec1 | 2.84 | +340 |
| W73A17 Rec2 | 4.92 | +670 |
| W73A17 Rec3 | 8.90 | +1300 |

These results relating to the increase in enzymic activity confirm those relating to the increase in the expression of the protein in the yeasts. They demonstrate that alteration of the 5' end alone, even when limited (Rec1), is sufficient to obtain a very substantial improvement in the production of the enzyme by the yeast and in its enzymic activity.

EXAMPLE 4

Expression of Wheat CYP86A5 in the Altered Yeasts

The sequence encoding wheat cytochrome P450 CYP86A5, which is depicted by sequence identifier No. 10 (SEQ ID No. 10 which encodes the amino acid sequence of SEQ. ID NO: 19), was isolated from the wheat cDNA library describer in Example 1 using the same method of operation as described for the CYP73A17 sequence and employing the complete coding sequence of *Arabidopsis thaliana* CYP86A1 as the probe. This wheat CYP86A5 sequence was altered, in accordance with the mode of operation of Example 2, using the two oligonucleotides depicted by the sequences ID No. 12 and 13 (SEQ ID No. 12 and SEQ ID No. 13) as sense and reverse primers, respectively, in order to obtain the coding sequence which is altered in accordance with the invention and which is depicted by sequence identifier No. 14 (SEQ ID No. 14(which encodes the amino acid sequence of SEQ. ID NO: 20).

A primer depicted by SEQ ID No. 11 was also used to enable yeasts to be transformed with the sequence encoding unmodified (native) wheat CYP86A5.

The yeasts are transformed with this new coding sequence and the expression is quantified by differential spectrophotometry in accordance with the mode of operation described in Example 2. While the natural sequence of wheat CYP86A5 is not expressed in a detectable manner, there is substantial expression in the transformed yeasts of the sequence which has been modified in accordance with the invention.

The above-described examples demonstrate unambiguously that the expression in yeasts of DNA sequences which possess a 5' region having a high content of codons which are poorly suited to yeasts is substantially improved when this region alone is simply recoded in accordance with the invention, ever partially, with corresponding codons which are well-suited to yeasts.

What is claimed is:

1. A recombinant non-yeast DNA encoding a plant protein of interest, wherein an unmodified DNA corresponding to said recombinant non-yeast DNA contains a region having a high content of codons that are poorly suited to for expression in yeasts, wherein at least 75% of the codons that are poorly suited for expression in yeasts are replaced in said region of said recombinant non-yeast DNA with synonymous codons coding for the same amino acid that are well-suited to for expression in yeasts, and wherein the number of replaced codons is sufficient to permit expression of the non-yeast DNA in yeasts.

2. The recombinant non-yeast DNA of claim 1, wherein 100% of the codons that are poorly suited for expression in yeast are replaced in said region of said recombinant non-yeast expression in yeasts, wherein the number of replaced codons is sufficient to permit expression of the non-yeast DNA in yeasts, and wherein the plant protein of interest is produced.

3. The recombinant non-yeast DNA according to claims 1 or 2, wherein the poorly suited codons are selected from the group consisting of codons whose frequency of use by yeasts is less than about 13 per 1000 codons.

4. The recombinant non-yeast DNA according to claim 3, wherein the protein of interest is an enzyme.

5. The recombinant non-yeast DNA according to claim 2, wherein the poorly suited codons are selected from the group consisting of CTC, CTG and CTT, which encode leucine, CGG, CGC, CGA, CGT and AGG, which encode arginine, GCG and GCC, which encode alanine, GGG, GGC and GGA, which encode glycine, and CCG and CCC, which encode proline.

6. The recombinant non-yeast DNA according to claim 5, wherein the poorly suited codons are selected from the group consisting of CTC and CTG, which encode leucine, CGG, CGC, CGA, CGT and AGG, which encode arginine, GCG and GCC, which encode alanine, GGG and GGC, which encode glycine, and CCG and CCC, which encode proline.

7. The recombinant non-yeast DNA according to claim 3, wherein the codons that are well-suited for expression in yeasts are selected from the group consisting of codons whose frequency of use by yeasts is greater than 15 per 1000 codons.

8. The recombinant non-yeast DNA according to claim 7, wherein the well-suited codons are selected from the group consisting of TTG and TTA, which encode leucine, AGA, which encodes arginine, GCT and GCA, preferably GCT, which encode alanine, GGT, which encodes glycine, and CCA, which encodes proline.

9. The recombinant non-yeast DNA according to claim 3, wherein the region having a high content of codons that are poorly suited for expression in yeasts contains at least 2 poorly suited codons among 10 consecutive codons, wherein the poorly suited codons are adjacent or nonadjacent to each other.

10. The recombinant non-yeast DNA according to claim 9, wherein the region having a high content of poorly suited codons contains 2, 3, 4, 5 or 6 poorly suited codons per 10 consecutive codons, or contain at least 2 or 3 adjacent poorly suited codons.

11. The recombinant non-yeast DNA according to claim 3, wherein the corresponding unmodified DNA is selected from the group consisting of a dicotyledonous plant DNA and a monocotyledonous plant DNA.

12. The recombinant non-yeast DNA according to claim 11, wherein the corresponding unmodified DNA is selected from the group consisting of a wheat DNA, a barley DNA, an oat DNA, a rice DNA, a maize DNA, a sorghum DNA, and a cane sugar DNA.

13. The recombinant non-yeast DNA of claim 3, wherein an unmodified DNA corresponding to said recombinant non-yeast DNA contains a region of high CTC codon or high CTC+CTG codon content, wherein a number of said CTC codons and/or CTG codons are replaced in said recombinant non-yeast DNA with TTG and/or TTA codons, and wherein the number of replaced codons is sufficient to permit expression in yeasts.

14. The recombinant non-yeast cDNA according to claim 13, wherein the CTC codon(s) and/or the CTG codon(s) are replaced with TTG codon(s).

15. The recombinant non-yeast cDNA according to claim 13, wherein the region having a high CTC codon or high CTC+CTG codon content encodes a polypeptide that contains 2, 3, 4, 5 or 6 leucines per 10 consecutive amino acids, or contain at least 2 or 3 adjacent leucines.

16. A chimeric gene which comprises a recombinant non-yeast DNA sequence according to claim 3 operably linked to heterologous 5' and 3' regulatory elements which are able to function in a yeast.

17. A yeast transformation vector comprising at least one chimeric gene according to claim 16.

18. A process for transforming a yeast cell using a vector according to claim 17 comprising contacting a yeast cell with said vector under conditions that permit said yeast cell to take up said vector.

19. A transformed yeast for expressing a protein of interest, comprising the chimeric gene according to claim 16.

20. A The yeast according to claim 19, which is selected from the group consisting of Saccharomyces, Kluyveromyces, Hansenula, Pichia and Yarrowia.

21. A process for producing a heterologous protein of interest in a transformed yeast, comprising:
   a) transforming a yeast with a vector which contains a recombinant non-yeast DNA according to claim 3 operably linked to heterologous 5' and 3' regulatory elements which are able to function in a yeast;
   b) culturing the transformed yeast; and
   c) extracting the protein of interest from the yeast culture.

22. A process for transforming a substrate by enzymatic catalysis with an enzyme which is expressed in a yeast comprising:

a) culturing, in the presence of the substrate to be transformed, a transformed yeast that expresses a protein of interest, said transformed yeast comprising a chimeric gene, said chimeric gene comprising a recombinant non-yeast DNA encoding a plant protein of interest, wherein an unmodified DNA corresponding to said recombinant non-yeast DNA contains a region having a high content of codons that are poorly suited for expression in yeasts, wherein a number of the codons that are poorly suited to yeasts are replaced in said region of said recombinant non-yeast DNA with synonymous codons coding for the same amino acid that are well-suited to yeasts, and wherein the number of replaced codons is sufficient to permit expression of the non-yeast DNA in yeasts, said chimeric gene being operable linked to heterologous 5' and 3' regulators elements which are able to function in a yeast; and b) recovering the transformed substrate from the yeast culture.

23. A recombinant non-yeast DNA encoding a plant protein of interest, wherein an unmodified DNA corresponding to said recombinant non-yeast DNA contains a region having a high content of codons that are poorly suited for expression in yeasts, wherein a number of the codons in the 5' region of the DNA that are poorly suited for expression in yeasts are replaced in said 5' region of said recombinant non-yeast DNA with synonymous codons coding for the same amino acid that are well-suited for expression in yeasts, wherein the number of replaced codons is sufficient to permit expression in yeasts, and wherein replaced codons are only in the 5' region.

24. A recombinant non-yeast DNA encoding a plant cytochrome P450, in which the non-yeast DNA encoding the plant cytochrome, P450 contains a region having a high content of codons that are poorly suited for expression in yeasts, wherein a number of the codons that are poorly suited for expression in yeasts are replaced in said region of said recombinant non-yeast DNA with synonymous codons coding for the same amino acid that are well-suited for expression in yeasts, such that the number of replaced codons is sufficient to permit expression of the plant cytochrome P450 DNA in yeasts.

25. The recombinant non-yeast DNA according to claim 24, wherein the corresponding unmodified DNA has a nucleotide sequence selected from the group consisting of SEQ ID NO:1 and SEQ ID NO:10.

26. The recombinant non-yeast DNA according to claim 24 having a nucleotide sequence selected from the group consisting of SEQ ID NO:7, SEQ ID NO:8, SEQ ID NO:9, and SEQ ID NO:14.

* * * * *